(12) United States Patent
Grace et al.

(10) Patent No.: US 6,431,009 B2
(45) Date of Patent: *Aug. 13, 2002

(54) DYNAMIC SHEAR TEST SAMPLE AND METHOD

(76) Inventors: Fred I. Grace, 90 Churchill Dr., York, PA (US) 17403; Rupert L. Nevin, 2820 Beckon Dr., Edgewood, MD (US) 21040; Lawrence E. Murr, 276 Amelia Dr., El Paso, TX (US) 79912

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,714

(22) Filed: Jan. 8, 1999

(51) Int. Cl.$^7$ .................................................. G01N 3/24
(52) U.S. Cl. ........................................................ 73/841
(58) Field of Search ........................... 73/842, 844, 841, 73/843, 845, 846, 7, 575, 666; 33/631, 645, 628, 632; 102/506, 507, 502

(56) References Cited

U.S. PATENT DOCUMENTS

| | | | | |
|---|---|---|---|---|
| 4,418,563 A | * | 12/1983 | Kalthoff et al. | 73/844 |
| 4,777,883 A | * | 10/1988 | Chevich | 102/503 |
| 4,845,995 A | * | 7/1989 | Kaste et al. | 73/841 |
| 5,712,431 A | * | 1/1998 | Vilendrer | 73/846 |
| 5,861,573 A | * | 1/1999 | Pickard | 102/506 |
| 6,148,533 A | * | 11/2000 | Hutter | 33/645 |

\* cited by examiner

*Primary Examiner*—Benjamin R. Fuller
*Assistant Examiner*—Octavia Davis
(74) *Attorney, Agent, or Firm*—W. Warren Taltavull; Manelli, Denison & Selter PLLC

(57) ABSTRACT

A method and apparatus for creating dynamic shear within metallic and non-metallic test sample materials under controlled conditions related to high ballistic impact includes the use of test sample having an end face with non-symmetrically placed surfaces extending away from a leading edge of the end face.

17 Claims, 9 Drawing Sheets

DYNAMIC SHEAR TEST SAMPLE AND METHOD

FIELD OF THE INVENTION

The present invention relates to characterization of material physical properties, and in particular, methods to dynamically induce shear in material samples at high strain rates and under conditions similar to those during very high velocity impacts, dynamic interactions, and penetration into targets. This invention further relates to techniques to perform metallurgical observation of sheared regions within the samples, testing of samples and subsamples containing the sheared regions, analytical modeling of the dynamic shearing process and development of associated constitutive relations.

DESCRIPTION OF THE PRIOR ART

Conventional dynamic shear testing apparatus used to generate high strain rate property data primarily include Kolsky Bar Impact, Split-Hopkinson Bar Impact and Pressure-Shear Plate Impact techniques. In addition, however, various non-standard techniques have been used for specific purposes and some of these have been summarized in the literature by Meyers and Murr. With several of these techniques, the material sample can be subjected to high strain rates associated with impacts only up to the lower end of ordnance velocity (<1000 m/s). In a number of such tests, the temperature can be set in advance by heating the sample prior to impact. This method artificially creates a temperature that has little relation to the adiabatically induced temperatures that are generated at strain rates and compression levels during very high velocity impact and penetration. Although somewhat high pressures can be arranged for within the Hopkinson Bar and Pressure-Plate Impact techniques, there are severe limitations. For example, generally, the magnitudes and time duration of the pressure pulses resulting from the impact are functions of the apparatus and thus are severely limited by impact velocity, compression wave speeds within the sample material and sample dimensions. Further, the pressure levels, pulse lengths, and strain rates are generally far below those associated with very high velocity impact and penetration. Not only are the conditions at higher velocity impacts (>1500 m/s) not attainable, but also, the sample material is not simultaneously subjected to the high levels of dynamic pressure, temperature and rates of strain that commonly and naturally arise during ballistic impact and penetration.

Various laboratory techniques have been developed for observing and characterizing the shear zones within sheared samples. These techniques have included mechanical property tests of the bulk samples containing shear zones and metallography. With these techniques, often multiple sets of individual shears and/or regions of combined shears are examined together, such that only bulk properties rather than those of the individual shear are determined. Further, the prior art techniques most likely create shears within the sample whose directions are often at random, unknown, or in non-preferred directions.

In the past, the modeling of sheared material necessarily attempted to describe mechanical properties of the bulk material. Thus, such models as Johnson and Cook, for example, are macroscopic and require extensive measurements of many coefficients to cover the many variables associated with the number of sheared areas, multiplicity of shears within an area, shear-shear interactions, variations with impact conditions, average orientation of the shear, and distributions about the averages. Generally, these details are not known within the macroscopic framework of the model.

The existing constitutive models are based on properties of the bulk material in the macroscopic sense. While such models as proposed in Johnson and Cook include material yielding criteria, strain-rate effects, temperature influences, thermal softening, and failure criteria, the associated coefficients are numerous and are empirically based. For a fully developed constitutive relation using the prior art, numerous, extensive and expensive tests, under impact conditions to include wide ranges of the above variables, must be conducted. Further, even with these complexities, resulting relations only approximate, often not very well, the actual response of the material subject to impact and penetration since loading conditions are most often radically different from those used to make the measurements.

SUMMARY OF THE INVENTION

The present invention provides for localized singular shear structures and shear regions to be created within the test sample during very high velocity impact and penetration. Thus, the associated strain rates, strains, pressures, and temperatures are concomitant and inherent as the shear takes place during the dynamic impact process. Further, the geometry is such that the shear direction with respect to a characteristic direction within the test sample is known and can be controlled during the impact. This present technique enables direct and unambiguous knowledge of the stress state within the sample during dynamic interaction with the receptor or target and the stress state's unambiguous relationship to the resulting shear. The details of observation conducted on recovered test samples allow for a microscopic characterization of single or multiple shears within the sample and, through subsection, allow for determination of post mechanical properties of the sheared material with respect to any desired shear orientation within the recovered sample material. The model addresses microscopic detail with generalization to a macroscopic description such that a more complete and applicable constitutive relation can be constructed.

To facilitate the shear characterization, modeling, and constitutive relation development, the geometries of the samples and impacted materials of the present invention are simulated with hydrocode computations using codes such as 2-D and 3-D CTH or Autodyn. Thus, the present invention provides for simulation of the dynamic impact using material elements in grid, cell or point mass form suitable for numerical solution. These calculations are conducted within the context of the invention to define impact experiments and associated material geometries. Further, application of the numerical computational process is used to define the stress states, strains, strain rate, pressures, temperatures, and the flow of the material during impact. The hydrocode computational process is applied iteratively at each stage of the dynamic shear characterization to analyze individual shear formation, behavior of shear zones, modeling of the phenomena, and development of constitutive relations.

It is therefore a primary object of this invention to provide a dynamic impact technique that can subject sample materials to shear along given directions within the sample and produce the shear under the conditions of strain rate, pressure, and temperature that exist during very high velocity impact- and penetration.

A second objective is to provide for post recovery examination of shear oriented samples and subsamples to determine basic material shear response to the loading conditions imposed on the sample under the conditions of impact and dynamic interaction with the receptor.

A third objective is to provide for a micromechanical model of the shear mechanism, instability, and material failure to facilitate accuracy of the description and lessen its cost.

A fourth object is to provide for geometric descriptions of the materials involved in the impact to include samples and receptors such that hydrocodes in 2-D and 3-D can be used to define tests, examine the loading conditions, calibrate the analytic models, and on an iterative basis, characterize the dynamic shearing to process, and develop constitutive relations for materials under dynamic loading conditions.

A still further object is to provide for an accurate and more applicable macroscopic constitutive relation to be used in ultimate descriptions of material response under dynamic loading. The techniques of the present invention lead to improved ability to conduct dynamic calculations, examine structural responses, assess crash worthiness, describe impact phenomena and ascertain important material properties for ballistic impact and penetration.

These and other objectives are achieved by designing a dynamic shear test that realistically simulates loading conditions created during high velocity impact, subjects the sample materials to shear and induces shear within the material at a given or chosen orientation. The shear test geometry consists of a test sample of varied geometry having a shaped surface with and without symmetry which is intended to be used in a high velocity impact test. The test sample is launched into a receptor material at various impact velocities of interest from ordnance velocity (<2000 m/s) up through the hypervelocity impact range (>2000 m/s).

Conversely, reverse ballistic tests are also used wherein the receptor material is launched into a standing test sample. The shear test geometry can also employ asymmetries within the receptor to induce the desired and specific shear within the test sample. The specific orientation of the individual shear and/or shear regions are characterized using recovered samples and subsamples cut at desired orientations with respect to the shear direction. Thus, the shear morphology and microscopic characterization are uniquely related to the loading conditions of the impact and dynamic interaction as previously described, and to the orientation of the shear. The macroscopic constitutive relation is developed from the microscopic characterization of the shear.

BRIEF DESCRIPTION OF THE DRAWINGS

FIG. 1c is a perspective view of the first embodiment of the test sample of the present invention shown in FIG. 1a.

FIG. 3d is a perspective view sample of the present invention shown in FIG. 3a.

DETAILED DESCRIPTION OF THE PREFERRED EMBODIMENTS

Figure 1A:
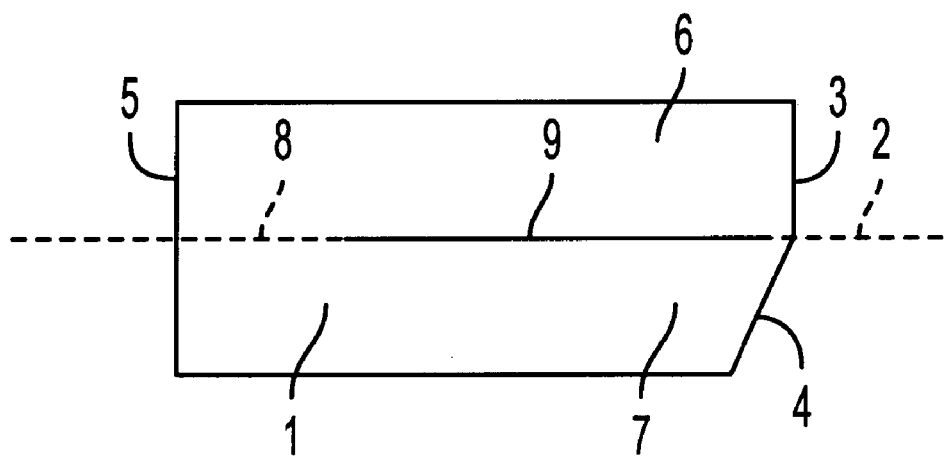
FIG. 1a is a longitudinal sectional view of a first embodiment of the test sample of the present invention.
Figure 1B:
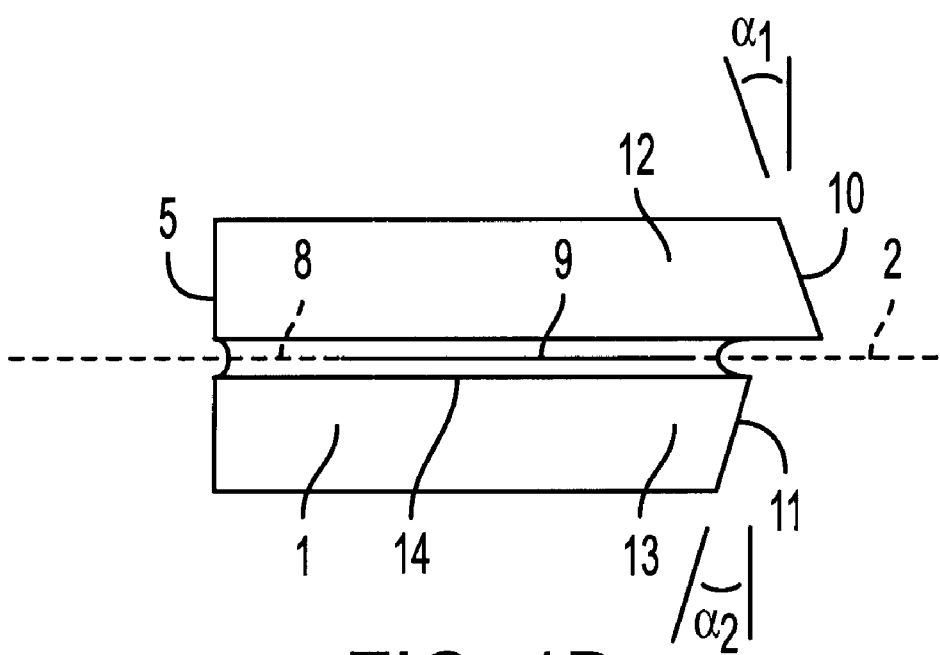
FIG. 1b is a longitudinal sectional view of a second embodiment of the test sample of the present invention.
Figure 1C:
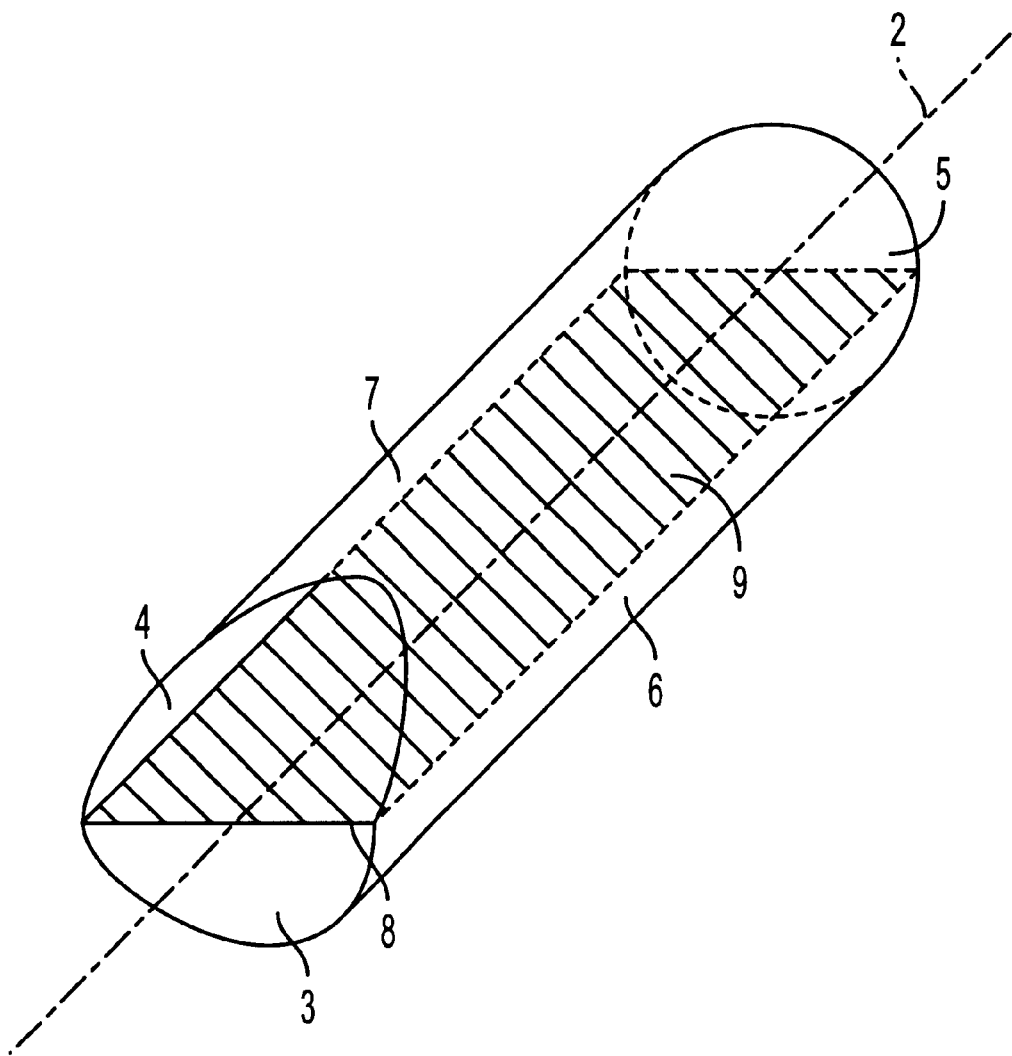

The test configuration for the dynamic shear characterization according to a first embodiment of the present invention is shown in FIGS. 1a and 1c. A test sample 1 is provided in cylindrical form about its flight, impact, or longitudinal axis 2 with an asymmetric frontal surface on one end which is intended to impact a receptor or target. The frontal surface is divided into a leading face 3 and a following face 4 where, upon impact, each face produces slightly different impact times and conditions. Upon impact, under normal conditions, with a symmetric frontal face, the test sample undergoes deceleration due to impact forces associated with the collision. At high impact velocity, the stress on the front of the test sample can exceed its strength so that erosion occurs in the frontal region of the sample material. However, even so, some time must lapse before the erosion of the front is fully established.

The body of the test sample 1 is acted upon by the forces of collision in the form of a series of stress waves that are transmitted from the frontal faces 3 and 4 to the sample rear surface 5 and reflected back again successively from rear surface 5 of the test sample 1. When the stress waves and their effects are integrated over time during impact, the net effect is deceleration of the test sample 1 body. The asymmetric front illustrated by faces 3 and 4 sets up initial but somewhat different conditions within the frontal sections 6 and 7 which are located directly behind the frontal faces 3 and 4. Thus, there are different decelerations of the test sample material immediately behind the leading section 6 and following section 7. In turn, motion of the two sections of the test sample differ in terms of deceleration, velocity, and displacement. In this manner, shear displacements between the leading section 6 and the following section 7 are generated.

The discontinuity at the intersection 8 between the faces 3 and 4 focuses the shear to take place on the shear plane 9 defined by the direction of the longitudinal axis 2 of the test sample 1 and the line defined by the intersection 8. The shear begins at or near the intersection 8 and propagates, in time, toward the rear Surface 5 of the test sample 1. As portions of the sheared frontal sections 6 and 7 are successively eroded away, the shear effect persists because of the differences in decelerations of sections 6 and 7. This condition promotes shear along the shear plane 9 which is manifested within the final uneroded portion of the remaining and recovered test sample.

The geometry of the test sample can be constructed to have various configurations of frontal faces and notches as shown in FIG. 1b. Here, the front of the test sample 1 is configured with tapered faces on each of the leading face 10 and following face 11. The angle $\alpha_1$ is associated with the leading or forward face 10 while angle $\alpha_2$ applies to the following or trailing face 11. The angles $\alpha_1$ and $\alpha_2$ can vary with respect to the normal direction of the test sample's axis 8. Further, the step 12 and notch 13 are used to provide a more pronounced discontinuity as a technique to focus shearing conditions on the test sample's shear plane 9. In addition, a notch 14 can be placed on the intersection of the shear plane 9 and the outer cylindrical surface of the test sample 1 to further focus shear. The tapers 10 and 11, step 12, notch 13, and notch 14 can be configured to have various dimensions and contours.

Figure 2A:
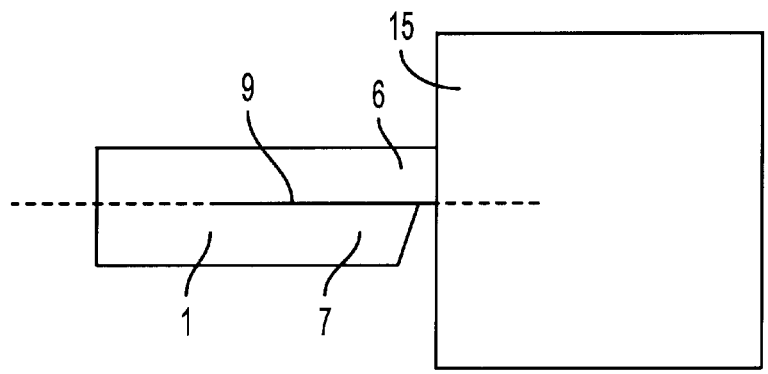
FIG. 2a illustrates initial contact of the test sample with the receptor front surface.

Initial phase of test sample impact with receptor is illustrated in FIG. 2a. Here, test sample 1 is shown at the instant of impact with the front surface of receptor 15 at normal incidence. The leading section 6 of the test sample 1 has just engaged the receptor 15 while the following section 7 has not yet reached the receptor 15. Thus, the impact forces are applied in this initial phase to the leading section 6 but not yet to the following section 7. Upon impact, in general, penetration into the receptor proceeds at a rate u which is initially about one half Of the test sample 1 impact velocity. The general deceleration for a rod undergoing erosion is given by Grace as:

$$M_p \frac{d(v-u)}{dt} = -A_p S_p, \qquad (1)$$

where $M_p$ is the mass of the eroding rod at any time t during the penetration, v is the rod velocity, $A_p$ is the cross-sectional area of the rod, and $S_p$ is the nominal strength of the rod material.

The mass of the rod at a particular time after impact is $M_p = \rho_p A_p l$, where l is the rod's current length and $\rho$ is the density of the rod, or in this case that of test sample 1. The erosion rate is $dl/dt = -(v-u)$ so that integration of equation (1) gives the velocity v of the test sample 1 in terms of its uneroded remaining length l relative to its initial length $l_o$, as $$v - u_o = (v_s - u_o)\left[1 + \frac{2S_p}{\rho_p(v_s - u_o)^2}\ln\left(\frac{l}{l_o}\right)\right]^{1/2}, \qquad (2)$$

where $u_o$ is the initial rate of penetration into the receptor upon impact. Thus, applying equation (2) for the leading section only, for the moment, demonstrates that as a result of test sample 1 initial impact, the velocity $v_1$ of the leading section 6 will be less than the velocity $v_2$ of the following section 7 which has not yet impacted the receptor.

Figure 2B:
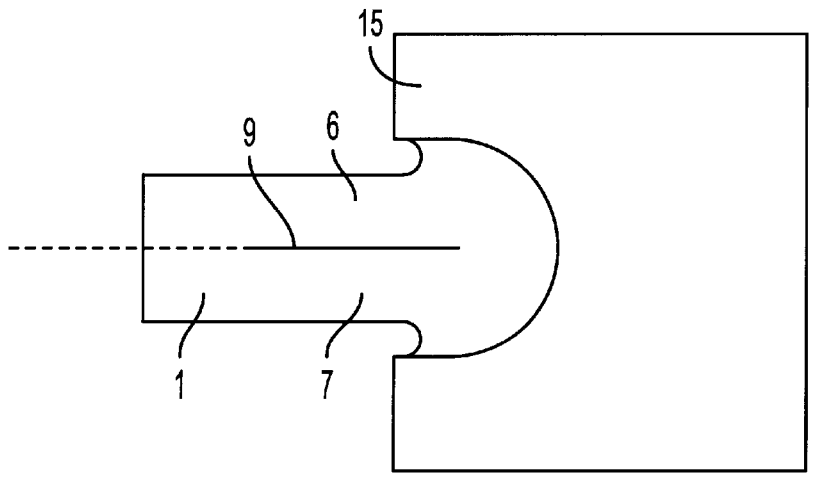
FIG. 2b is illustrative of the erosion and material flow of the test sample within the receptor.

After both sections have engaged the receptor 15, as shown in FIG. 2b, the velocity difference persists. The following section 7 will be decelerated to a velocity $v_2$ which always will be greater than the velocity $v_1$ of the leading section 6 because of the initial delay between impacts of the two sections. Furthermore, the dynamics of the situation as reflected by equation (2) suggest that the difference between the two velocities tends to increase as the rod erodes. Also, there will be an opposite tendency for the two sections 6 and 7 to approach the same velocity due to the strength of the material of the test sample 1. Consequently, the net difference in motion of the two sections 6 and 7 is determined by the shear properties of the material along the sheer stress plane 9. Initially, just before the following section 7 impacts the receptor, $v_2 = v_s$. At this point, equation (2) gives the difference in velocity of the two sections as $$v_s - v_1 = (v_s - u_o)\left[1 - \left(\left[1 + \frac{2S_p}{\rho_p(v_s - u_o)^2}\ln\left(\frac{1}{l_o}\right)\right]\right)^{1/2}\right]. \qquad (3)$$

The difference in velocity of the two sections gives rise to shear strain along the shear plane 9. Defining a thickness for the sheared material on the shear plane 9 as $s_o$ gives the shear strain rate $\dot{\gamma}$ and an initial estimate of the shear strain $\gamma$ as:

$$\dot{\gamma} = \frac{v_s - v_1}{S_o}, \gamma = \frac{v_s - v_1}{S_o}t, \qquad (4)$$

where t is the elapsed time after impact. The strain and strain rates are estimated throughout the impact and dynamic interaction processes by numerical solution of the velocity equation (2) as applied independently to the two sections of the test sample.

Figure 2C:
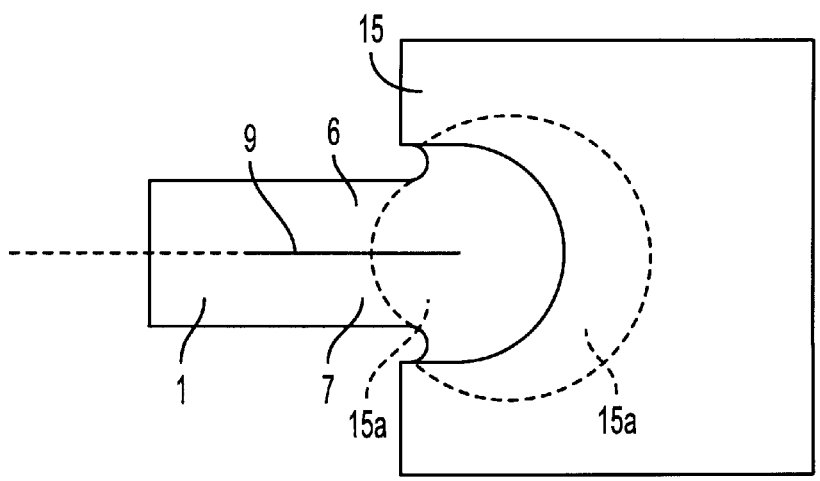
FIG. 2c illustrates the development of stress fields within the test sample and the receptor.

FIG. 2c depicts the stress encountered by the test sample 1 during penetration into the receptor 15. The stress at the front of the test sample 1 is given by the pressure of stagnation of the receptor material flowing into the centerline of the frontal surface and is estimated from the Bernoulli equation as $$P = 1/2 \rho_t U^2, \qquad (5)$$

where P is the pressure, $\rho_t$ is the density of the receptor material, and u is the penetration reate of the test sample 1 into the receptor 15. A stress field 15a develops both within the receptor material adjacent to the test sample front and within the frontal sections of the test sample 1, as well. Associated with the pressure or stress field is an increase in temperature due to adiabatic heating during compression of the sample under the stress field 15a. Thus, the technique produces shear strain under the conditions of high strain rate, compression, and temperature that is associated with the dynamic interaction. These variables are controlled by material properties of test sample 1 and receptor 15 and the impact conditions such as initial densities, nominal material strengths and impact velocity.

Figure 3A:
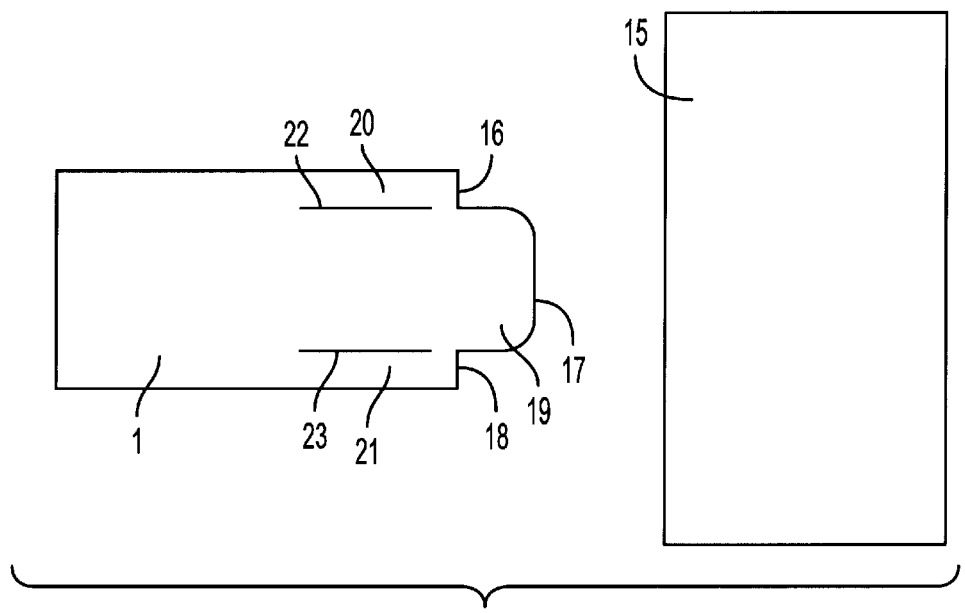
FIG. 3a is a longitudinal sectional view of a third alternate embodiment of the test sample of the present invention.
Figure 3C:
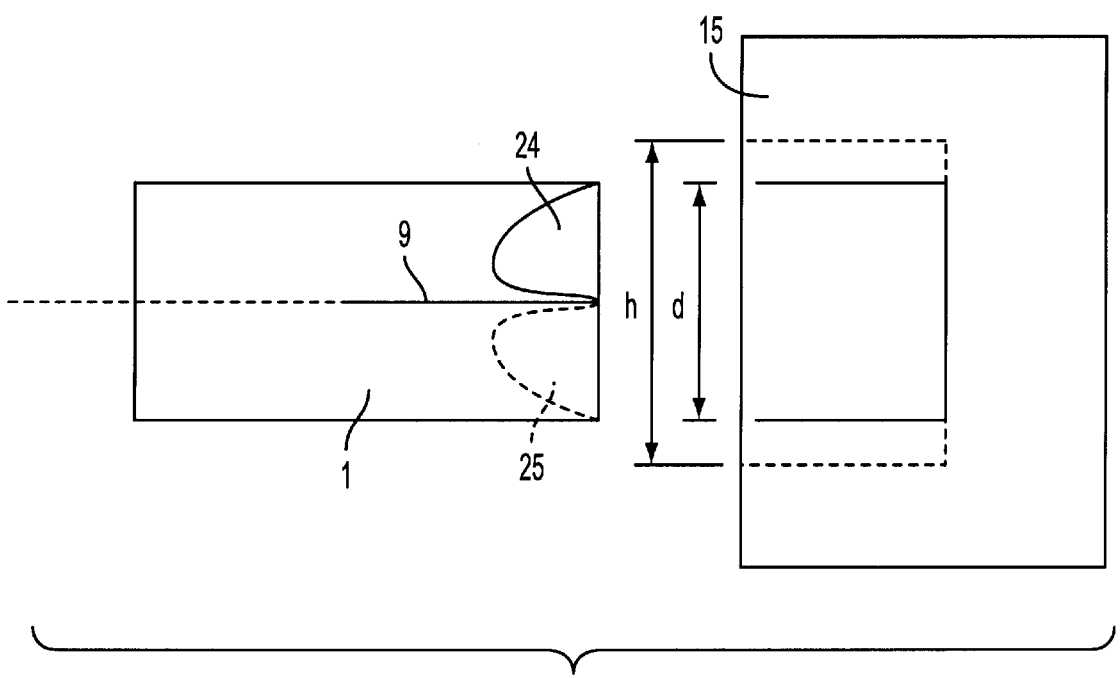
FIG. 3c is a longitudinal sectional view of a fifth alternate embodiment of the test sample of the present invention.
Figure 3B:
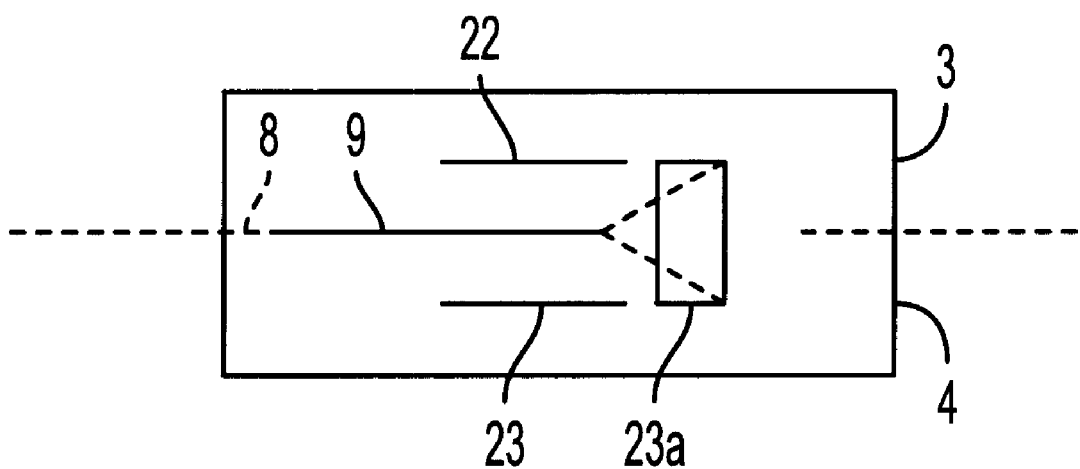
FIG. 3b is a longitudinal sectional view of a fourth alternate embodiment of the test sample of the present invention.
Figure 3D:
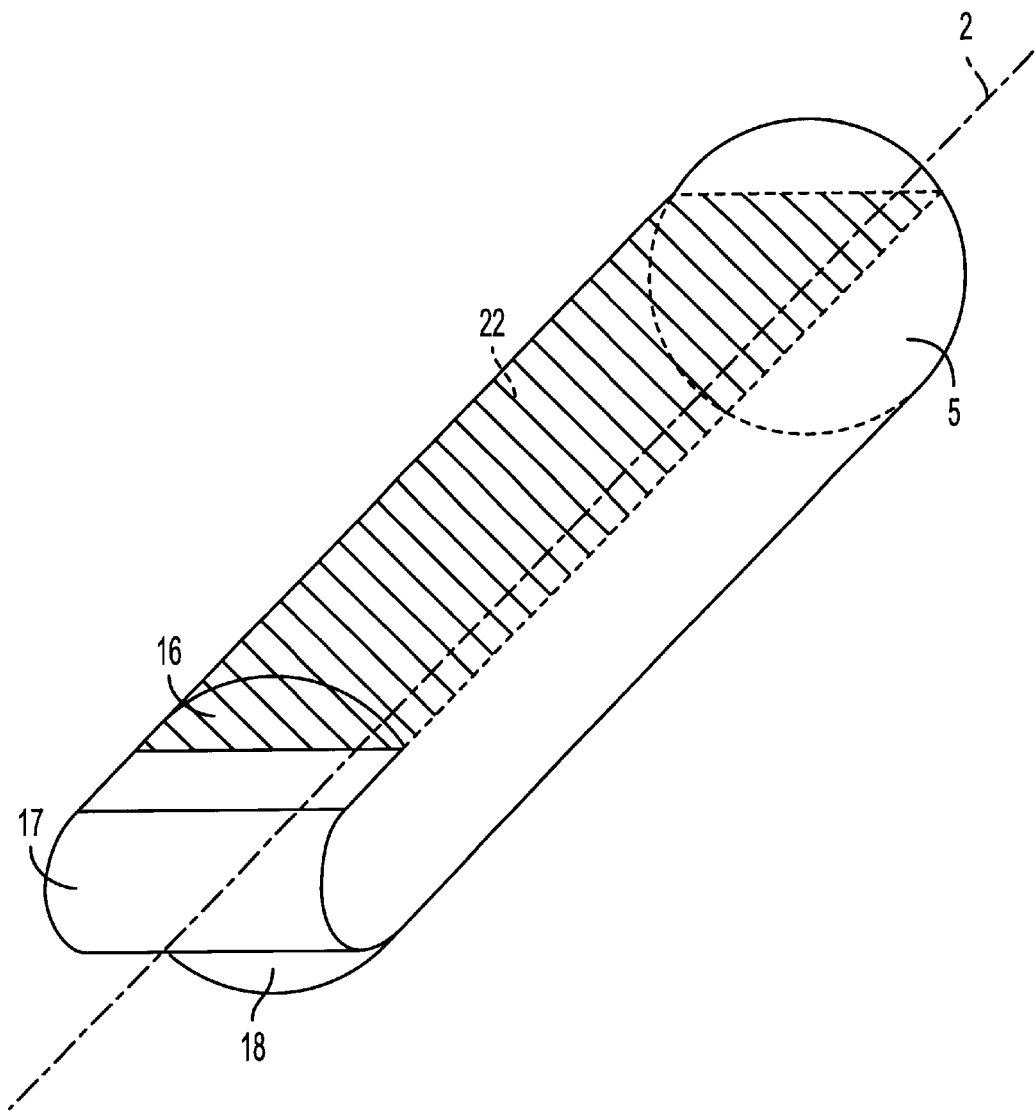
Figure 3E:
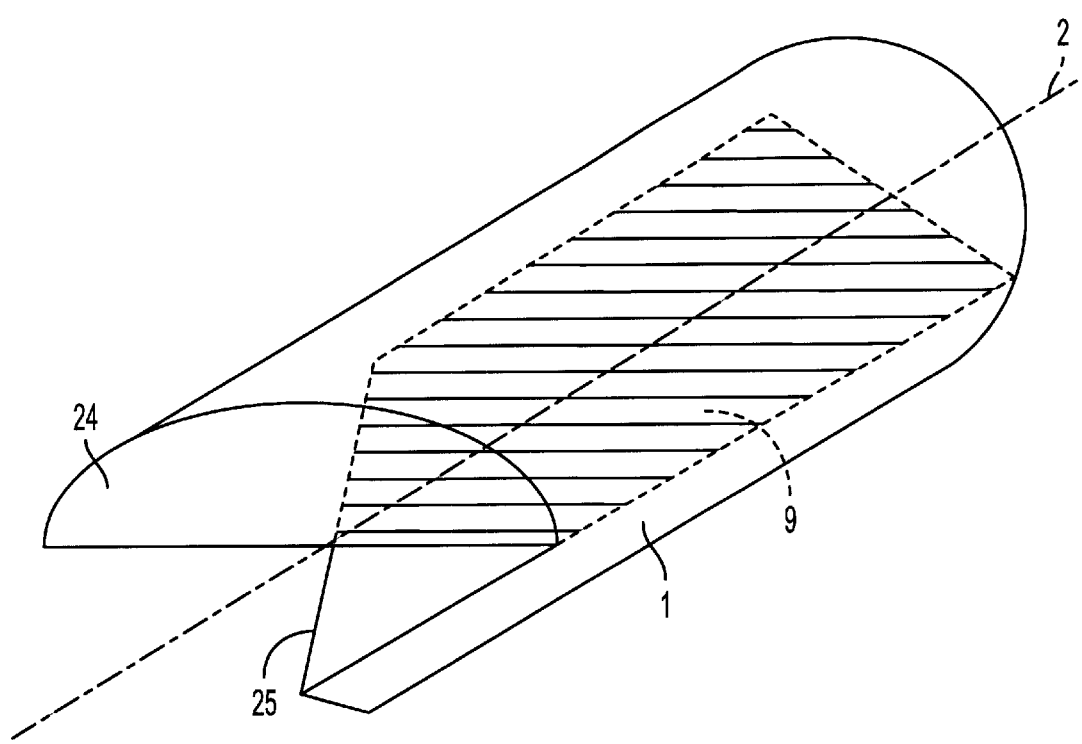
FIG. 3e is a perspective view of another embodiment of the invention.

A third embodiment, shown in FIGS. 3a and 3d, provides for a double set of shear planes to be created within the test sample 1 during dynamic interaction with the receptors 15. With this embodiment, three frontal faces and associated sections are utilized. A typical configuration provides for an upper face 16, a center face 17, and a lower face 18. As shown, the associated center section 19 leads the impact while the associated upper and lower sections 20 and 21 follow. During dynamic impact, an upper shear plane 22 and a lower shear plane 23 are created. The analysis is similar to that described above but now three sections and two sets of relative velocities are present. The specific shears generated on each of the shear planes 22 and 23 are controlled by the relative dimensions of the frontal features, as before. Thus, in this embodiment, various frontal configurations can be employed, and also the center section 19 can be configured to follow the upper and lower sections 16 and 18 by locating the center face 17 closer to the rear of test sample 1 in opposite fashion to that shown in FIG. 3a. When the frontal section follows the outer sections during impact, the shear strain on shear planes 16 and 18 is produced in an opposite direction to that produced when the frontal section leads the impact.

A fourth embodiment, as a means to produce shear strain on shear planes 22 and 23 or to focus shear on shear plane 9 is shown in FIG. 3b. The body of the test sample can be configured to have single or multiple bores or slots passing through it in a general direction perpendicular to the axis of symmetry 8. Accordingly, the test sample 1 contains a slot 23a located along the axis of symmetry 8 but behind leading faces 3 and 4. With this embodiment, the frontal faces could be portions of an orthogonal plane transverse to the axis of symmetry 8. The asymmetry of impact in this case is created not by the frontal surfaces, but subsequent effect of slot 23a during penetration. The configuration of slot 23a determines whether multiple shear planes 22 and 23 are produced as shown in FIG. 3a or whether the shear is focused on shear plane 9 as shown in FIG. 1a. When the trailing edge of slot 23a comes to near point, then shear plane 9 is activated, otherwise shear planes 22 and 23 result.

Figure 5:
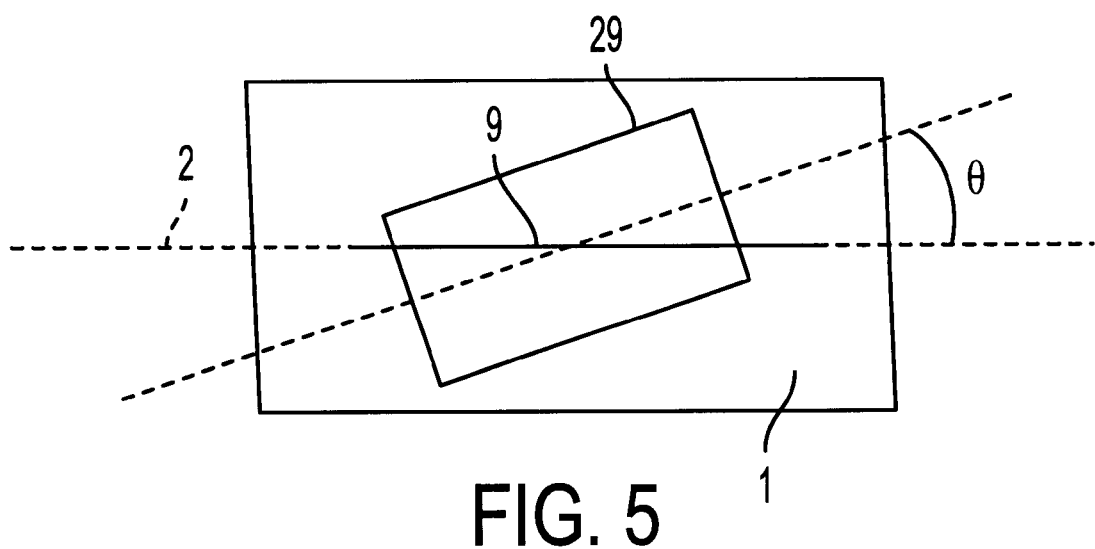
FIG. 5 is illustrative of the sectioning of subsamples from the recovered test sample resulting in known shear directions.

A fifth embodiment, as a means to produce shear strain within shear plane 9 but at a transverse direction to the axis of the test sample, is shown in FIGS. 5, 3b and 3d. The frontal configuration of the test sample 1 not only has leading and following faces but includes tapers whose planes intersect with the transverse plane of the test sample 1 along the vertical. These tapers contrast with those of the second embodiment which intersect along the horizontal. The taper of the upper section 24 is opposite to that of the lower section 25. The net effect of the two sections is to steer the upper and lower sections in two opposite transverse directions during dynamic interaction of the test sample 1 with the receptor 15. The amount of transverse deflection, as observed within the recovered receptor 15, determines the amount of transverse shear created within the test sample 1. If the usual diameter of the crater path in the receptor is designated d and the observed cavity width is h, then the transverse shear $\gamma_t$ can be determined. Further, when the cavity is expanding at a rate dh/dt and $\beta$ is the angle at which expansion takes place with respect to the path axis within receptor 15, then the transverse shear and shear strain rate, respectively, are $$\gamma_t = \frac{h-d}{S_o}, \gamma_t = \frac{u_o}{S_o}\tan(\beta), \qquad (6)$$

where $s_o$ is again the thickness of the sheared region.

Figure 4A:
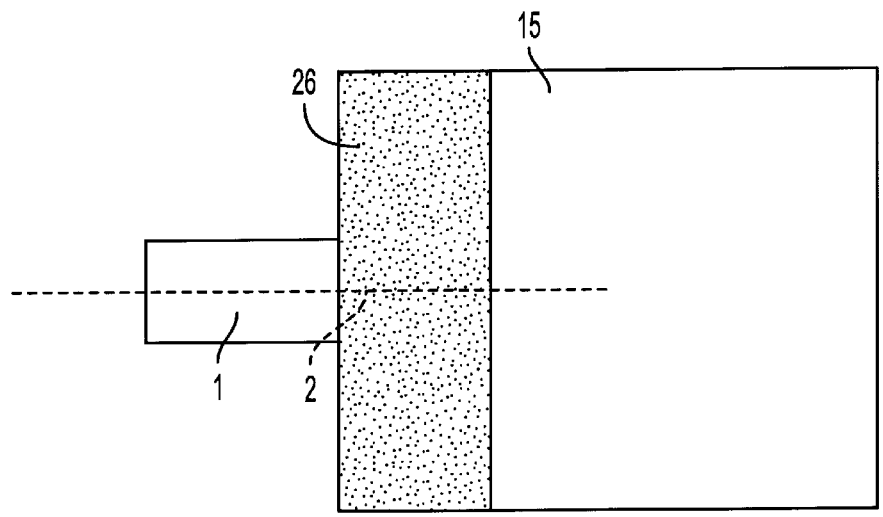
FIG. 4a is a longitudinal sectional view of the test sample, dynamic conditioning element, and backup receptor according to a sixth embodiment of the present invention.

FIG. 4a shows a fifth preferred embodiment that provides for dynamic shear formation within the test sample 1 during dynamic interaction by introducing a conditioning element 26 placed in front of the receptor 15. With this technique, the test sample 1 impacts the conditioning element 26 which can be backed up by the usual receptor 15. The purpose of the conditioning element 26 is to development an asymmetric flow at the front of the test sample 1 even though its frontal shape may or may not be asymmetrical and employ notches, as before. The material within the conditioning element 26 is arranged to be nonhomogeneous. The conditioning element 26 can have many subcomponents without geometric and mechanical symmetry or with symmetry not about the test sample's flight direction 2. Thus, upon impact, the test sample 1 experiences a nonsymmetric stress field acting on its frontal portions. The amount of asymmetry and/or orientation of the components within the conditioning element establishes the magnitude of longitudinal and lateral force imbalances applied to the test sample 1 which provide the test sample with a subsequent tendency to rotate about or translate with respect to the ideal flight line 2.

Figure 4B:
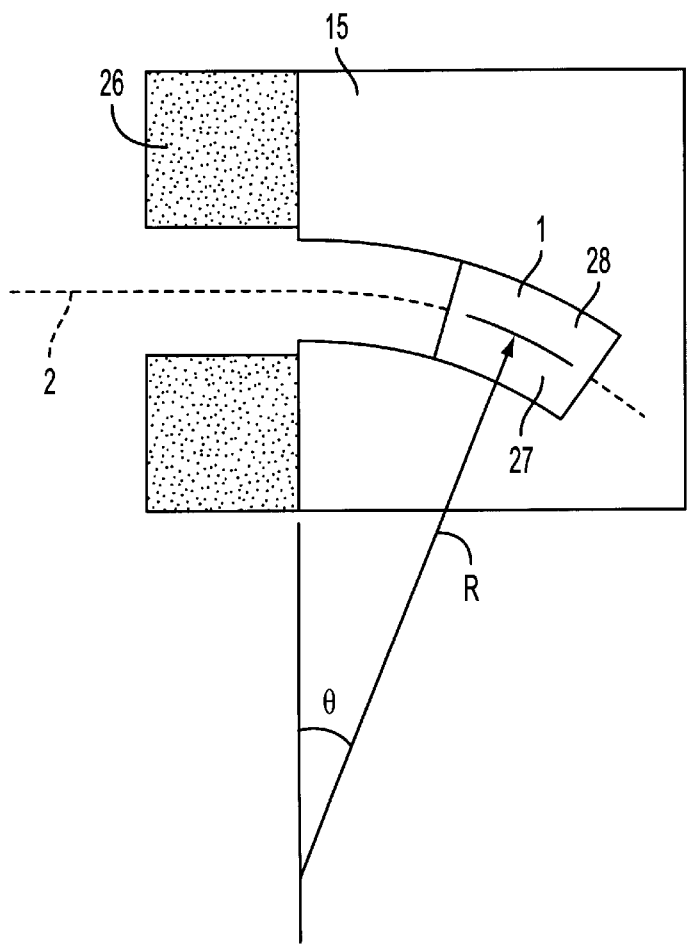
FIG. 4b illustrates the curved path taken by the test sample within the receptor.

After passing into conditioning element 26, a curved path can be taken by the test sample 1 within the backup receptor 15 as shown in FIG. 4b. When the test sample 1 is visualized again as being composed of two sections, then the two sections now are an intersection 27 and an outer section 28 with respect to the center of radius R of the curved path. The two sections encounter different amounts of receptor material during advancement along the path which is created by the dynamic interaction. Also, the advancement rates, decelerations, and displacements of the outer section 28 and the inner section 27 are different. If the centerline 2 of the test sample 1 enters the receptor 15 with an advancement rate $u_o$, then the centers of mass along the radius for the outer and inner sections 28 and 27 can have advancement $u_2$ and $u_1$, respectively, where the advancement rate $u_o$ is related to the radius of curvature R of the path and the subtended angle according to $$u_o = R\frac{d\theta}{dt}. \qquad (7)$$

If, for the sake of argument, the sections each represent one half of the total, then the centers of the areas for the outer and inner sections 28 and 27 are displaced from the test sample's centerline by an amount $$c = \frac{4}{3\pi}R, \qquad (8)$$

which results in a difference in advancement rates for the two sections 28 and 27, respectively, as $$u_2 = \left(\frac{R+c}{R}\right)u_o, u_1 = \left(\frac{R-c}{R}\right)u_o, \qquad (9)$$

where the differences in $u_2$ and $u_1$ show up as differences in test sample velocity $v_2$ for the outer section 28 and $v_1$ for the inner section 27 when $u_2$ and $u_1$ are substituted into equation (2) for $u_o$. As before, the difference in velocity gives rise to shear strain development on shear plane 9 while the test sample 1 takes the curved path associated with the dynamic interaction of test sample 1 and receptor 15. Knowing $v_2$ and $v_1$ from the radius of curvature allows the use of equation (4) to determine the strain and strain rate for this technique. The strain and strain rate along the entire path is obtained as a function of $u_o$ and $\theta$ through numerical solution of equation (2) when equations (7) and (9) are employed.

The embodiments described provide for stress or pressure fields to be applied to the test sample during dynamic interaction with the receptor. For high velocity impacts, the test sample erodes in the frontal region since the stresses exceed the strength of the sample material. However, just behind the front surface, but within the test sample body, the stress drops off monotonically with distance from the front surface. While the stresses can exceed material strength at the front of the test sample, they do not within the sample body. For most materials, the shear strength is smaller than the yield strength. Thus, while the pressure falls below the yield strength within the body, the shear displacements occurring at lower stress levels can take place. The above embodiments take advantage of this situation to generate shear in the remaining portions or uneroded portions of the test sample.

These described embodiments can be utilized within both direct launch and reverse ballistic impacts. Test samples are recovered at the bottom of the path when the receptor is semiinfinite or can be soft recovered behind the receptor when a finite-thickness receptor is employed. Further, receptors of different thicknesses can be used to control the amount of erosion and therefore the length of the recoverable test sample which emerges from the receptor rear surface. Thus, the amount of shear generated within the test sample, its character in terms of longitudinal or transverse direction and its location with respect to position within the test sample are also controlled.

The embodiments also cover the cases wherein the test sample advances into the receptor in rigid-body mode. In this case, the penetration rate is identical to the velocity of the test sample, but the asymmetrical loading by the dynamic interaction induces shear along the previously described interface between the two sections of the test sample. The primary difference in the eroding body case is the equation of deceleration not given by equations (I) and (2) above, but rather by a Poncelet type of retarding force such as $$M\frac{dv}{dt} = -a - bv^2, \tag{10}$$

having a solution of the form for the velocity v of the body as $$v = \sqrt{a/b} \tan(a \tan(\sqrt{a/b}v_s) - t\sqrt{ab}/M), \tag{11}$$

where a is a constant retarding force and b is a retarding factor associated with the velocity squared drag law. With equation (11) applied to each section of the test sample, differences in velocities are provided and the shear strain and strain rate analyses previously discussed apply.

The described embodiments are geometrically structured so that material masses are represented in grid, point mass, or cell for. The various geometrical details are represented often by separate subsections within the overall grid, for example. In particular, various material properties can be specified for each subsection, to include a shear description, within the computational process used in the 2-D and 3-D hydrocodes. Thus, the stress states during impact, strains, strain rates, pressures and temperatures can be determined to a great level of accuracy. The impact calculations of these embodiments, using an iterative process and varying material properties, lead to accurate descriptions of the loading conditions, shear formation, and response of the materials to dynamic loading.

The ability to induce shear at a given location and orientation within the test sample allows for preparation of subsamples having contained shear features of known orientation even though the shear may not extend to or be observed on the surface of the recovered test sample. As shown in FIG. 5, this ability facilitates metallurgical examination, mechanical property determinations, and the interpretation of results. The shear feature 9 and the body outline of the subsample 29 are shown in relation to the recovered test sample i. Thus, the subsample can be sectioned out of the sample at any desired angel $\phi$ so that the shear orientation with respect to the product subsample is uniquely defined even though it may not be observed on the surfaces of either sample or subsample.

High speed diamond sawing can extract thin wafers from this sample as described and these wafers can be ground and discs punched for electropolishing to electron transparent thin sections for transmission electron microscopy. These same wafers or wafer sections adjacent to the electron microscope discs can be mounted and polished for light metallography. This technique allows for parameters relating to the crystal lattice and the microstructures and microscopic and macroscopic damage to be determined uniquely in the sheared region. The basic issues of materials characterization using transmission electron microscopy and the preparation of thin sections from sawed wafers are described by Murr.

As described, the dynamic interaction analysis allows for a determination of applied conditions within the test sample at the location of the shear feature. These applied conditions include the dynamic interaction stress or pressure P, amount of shear stress $\tau$, temperature T, strain $\gamma$, strain rate $\dot\gamma$, shear orientation $\phi$, parameters related to the lattice and microstructures of the parent material L, and microscopic damage within the sheared regions Q. For a given sample material, these conditions vary with impact velocity. Thus, several tests using the described techniques of the present invention establish the desired model for dynamic shear characterization. Two elements of the shear characterization include the onset of shear in terms of a critical function $f_c$, and the effective shear strength $\tau_e$ within the sheared region as $$f_c = f(\tau, \tau_o, \gamma, \dot\gamma, \phi, T, P, L, Q) \geq 1, \tau_e = g(\tau_o, \gamma, \dot\gamma, \phi, T, P, L, Q) \tag{12}$$

where $\tau_o$, is the shear strength of the starting material. The constitutive relation for the bulk material whose properties have evolved with shear strain results from a summation of the shear descriptions developed within equation (12). To those skilled in the art, many modifications and variations of the present invention are possible in light of the above teachings. It is therefore to be understood that the present invention can be practiced otherwise than as specifically described herein and still will be within the spirit and scope of the appended claims.

We claim:

1. A test body for producing dynamic shear in the test body during high velocity impact on and penetration of an object, comprising a substantially cylindrical body portion having a first end and a second end and an axis of symmetry, said first end having a first face portion and a second face portion with one of said face portions being substantially planar and extending in a plane that intersects said axis of symmetry at an angle other than 90° to induce shear forces in said test body upon impact of said first end with a target, said second end constituting the rear end of said body portion.

2. The invention as claimed in claim 1 wherein said second face portion is substantially planar and extends in a plane different from said plane in which said first face extends and which also intersects said axis of symmetry of said body portion.

3. The invention as claimed in claim 2 wherein said first and second face portions intersect said axis of symmetry at substantially the same point on said axis of symmetry.

4. The invention as claimed in claim 2 wherein said first and second face portions intersect said axis of symmetry at points spaced apart on said axis of symmetry.

5. The invention as claimed in claim 1 wherein said other of said face portions intersects said axis of symmetry at 90°.

6. The invention as claimed in claim 4 wherein a gap is provided between said first and second faces and which extends along said axis of symmetry.

7. The invention as claimed in claim 1 wherein said first end is an impact end.

8. The invention as claimed in claim 1 wherein said body is made of metal material.

9. The invention as claimed in claim 1 wherein said body is made of non-metallic material.

10. The invention as claimed in claim 1 wherein said body is made of metal material.

11. The invention as claimed in claim 1 wherein said body is made of non-metallic material.

12. A test body for producing dynamic shear in the body upon impact with a target as claimed in claim 1, said target comprising a conditioning element and a receptor wherein said conditioning element is positioned on said receptor so that said body impacts first with said conditioning element.

13. The invention as claimed in claim 12 wherein said conditioning element is a non-homogeneous material.

14. The invention as claimed in claim 12 wherein said body is made of metallic material.

15. A method of using a test body for producing dynamic shear in the body comprising the steps of using a substantially cylindrical body portion having a first end and a second end and an axis of symmetry with said first end having two planar surfaces disposed asymmetrically relative to said axis of symmetry, and directing the body at a target such that said first end of the body impacts the target in a plane, the plane being perpendicular to the direction of travel of the body.

16. A method of using a test body comprising the steps of using a substantially cylindrical body having opposite ends and an axis of symmetry extending between said ends with one of said ends having at least two surfaces on opposite sides of said axis of symmetry and which extend from said axis of symmetry at different angles and directing the body at a target with said one of said surfaces impacting the target first.

17. A test member for producing dynamic shear in the member upon impact with a target, said member comprising a substantially cylindrical body having a first end a second end and an axis of symmetry extending between said ends, said first end having a first portion having a leading edge and a notch extending along the axis of symmetry of said body and a second portion which is set back from said leading edge of said first portion so that said leading edge of said first portion will contact said target first and induce shear forces in said test member in a selected direction wherein said second portion of said test member comprises a segment which extends in a plane that lies at an angle other than 90° to the axis of symmetry of the test member.

\* \* \* \* \*